US011654279B2

United States Patent
Wasserman et al.

(10) Patent No.: US 11,654,279 B2
(45) Date of Patent: May 23, 2023

(54) APPLYING TUMOR TREATING FIELDS (TTFIELDS) VIA ELECTRODES EMBEDDED INTO SKULL IMPLANTS

(71) Applicant: Novocure GmbH, Root (CH)

(72) Inventors: Yoram Wasserman, Haifa (IL); Uri Weinberg, Binyamina (IL); Zeev Bomzon, Kiryat Tivon (IL)

(73) Assignee: Novocure GmbH, Root (CH)

( * ) Notice: Subject to any disclaimer, the term of this patent is extended or adjusted under 35 U.S.C. 154(b) by 17 days.

(21) Appl. No.: 16/937,695

(22) Filed: Jul. 24, 2020

(65) Prior Publication Data

US 2021/0031031 A1    Feb. 4, 2021

Related U.S. Application Data

(60) Provisional application No. 62/880,893, filed on Jul. 31, 2019.

(51) Int. Cl.
*A61N 1/36* (2006.01)
*A61N 1/04* (2006.01)
(Continued)

(52) U.S. Cl.
CPC ....... *A61N 1/36002* (2017.08); *A61N 1/0488* (2013.01); *A61N 1/0529* (2013.01); *A61N 1/36017* (2013.01); *A61N 1/40* (2013.01)

(58) Field of Classification Search
CPC .............................. A61N 1/0488; A61N 1/0529
See application file for complete search history.

(56) References Cited

U.S. PATENT DOCUMENTS 5,983,141 A * 11/1999 Sluijter ................. A61N 1/403
607/100
6,868,289 B2    3/2005 Palti
(Continued)

FOREIGN PATENT DOCUMENTS

JP    2097501067 A    1/2007
WO    2005115535 A2    12/2005
(Continued)

OTHER PUBLICATIONS

Bomzon et al., "Using computational phantoms to improve the delivery of Tumor Treating Fields (TTFields) to patients," 38th Annual International Conference of the IEEE Engineering in Medicine and Biology Society (EMBC), IEEE, pp. 6461-6464, 2016.
(Continued)

*Primary Examiner* — Michael W Kahelin
(74) *Attorney, Agent, or Firm* — Potomac Law Group, PLLC

(57) ABSTRACT

Tumors inside a person's head (e.g., brain tumors) can be treated using tumor treating fields (TTFields) by positioning capacitively coupled electrodes on opposite sides of the tumor, and applying an AC voltage between the electrodes. Unlike the conventional approach (in which all of the electrodes are positioned on the person's scalp) at least one of the electrodes is implemented using an implanted apparatus. The implanted apparatus includes a rigid substrate shaped and dimensioned to replace a section of the person's skull. At least one electrically conductive plate is affixed to the inner side of the rigid substrate, and a dielectric layer is disposed on the inner side of the conductive plate or plates. An electrically conductive lead is used to apply an AC voltage to the conductive plate or plates.

14 Claims, 1 Drawing Sheet

(51) Int. Cl.
*A61N 1/05* (2006.01)
*A61N 1/40* (2006.01)

(56) References Cited

U.S. PATENT DOCUMENTS

| | | | |
|---|---|---|---|
| 7,016,725 B2 | 3/2006 | Palti | |
| 7,089,054 B2 | 8/2006 | Palti | |
| 7,136,699 B2 | 11/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,684,866 B2 * | 3/2010 | Fowler | A61N 1/36082 607/45 |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,777 B2 * | 5/2014 | Lowry | A61N 1/0531 607/45 |
| 10,188,851 B2 | 1/2019 | Wenger et al. | |
| 10,441,776 B2 | 10/2019 | Kirson et al. | |
| 10,779,875 B2 | 9/2020 | Palti et al. | |
| 10,821,283 B2 | 11/2020 | Giladi et al. | |
| 2003/0125786 A1 * | 7/2003 | Gliner | A61N 1/40 607/116 |
| 2006/0167499 A1 | 7/2006 | Palti | |
| 2007/0225766 A1 | 9/2007 | Palti | |
| 2007/0239213 A1 | 10/2007 | Palti | |
| 2008/0312716 A1 | 12/2008 | Russell | |
| 2009/0076366 A1 | 3/2009 | Palti | |
| 2012/0283726 A1 | 11/2012 | Palti | |
| 2014/0330268 A1 | 11/2014 | Palti et al. | |
| 2017/0120041 A1 | 5/2017 | Wenger et al. | |
| 2017/0215939 A1 | 8/2017 | Palti et al. | |
| 2017/0281934 A1 | 10/2017 | Giladi et al. | |
| 2018/0001075 A1 | 1/2018 | Kirson et al. | |
| 2018/0008708 A1 | 1/2018 | Giladi et al. | |
| 2018/0050200 A1 | 2/2018 | Wasserman et al. | |
| 2018/0117332 A1 | 5/2018 | Robinson et al. | |
| 2018/0160933 A1 | 6/2018 | Urman et al. | |
| 2018/0202991 A1 | 7/2018 | Giladi et al. | |
| 2019/0117956 A1 | 4/2019 | Wenger et al. | |
| 2019/0117963 A1 | 4/2019 | Travers | |
| 2019/0307781 A1 | 10/2019 | Krex et al. | |
| 2019/0308016 A1 | 10/2019 | Wenger et al. | |
| 2020/0001069 A1 | 1/2020 | Kirson et al. | |
| 2020/0009376 A1 | 1/2020 | Chang et al. | |
| 2020/0009377 A1 | 1/2020 | Chang et al. | |
| 2020/0016067 A1 | 1/2020 | Gotlib et al. | |
| 2020/0023179 A1 | 1/2020 | Bomzon et al. | |
| 2020/0061360 A1 | 2/2020 | Hagemann et al. | |
| 2020/0061361 A1 | 2/2020 | Hagemann et al. | |
| 2020/0069937 A1 | 3/2020 | Naveh et al. | |
| 2020/0078582 A1 | 3/2020 | Alon et al. | |
| 2020/0108031 A1 | 4/2020 | Borst et al. | |
| 2020/0121728 A1 | 4/2020 | Wardak et al. | |
| 2020/0129761 A1 | 4/2020 | Bomzon et al. | |
| 2020/0146586 A1 | 5/2020 | Naveh et al. | |
| 2020/0155835 A1 | 5/2020 | Wasserman et al. | |
| 2020/0171297 A1 | 6/2020 | Kirson et al. | |
| 2020/0179512 A1 | 6/2020 | Giladi et al. | |
| 2020/0219261 A1 | 7/2020 | Shamir et al. | |
| 2020/0254242 A1 | 8/2020 | Chang et al. | |
| 2020/0269037 A1 | 8/2020 | Hagemann et al. | |
| 2020/0269041 A1 | 8/2020 | Zeevi et al. | |
| 2020/0269042 A1 | 8/2020 | Giladi et al. | |
| 2020/0269043 A1 | 8/2020 | Wasserman et al. | |
| 2020/0306531 A1 | 10/2020 | Tran et al. | |
| 2020/0330755 A1 | 10/2020 | Wasserman et al. | |

FOREIGN PATENT DOCUMENTS

| | | | |
|---|---|---|---|
| WO | 2012063377 A1 | 5/2012 | |
| WO | 2018033842 | 2/2018 | |

OTHER PUBLICATIONS

International Search Report and Written Opinion issued in application No. PCT/IB2020/057022 dated Oct. 20, 2020.
Korshoej et al., "Enhancing Predicted Efficacy of TumorTreating Fields Therapy of Glioblastoma Using Targeted Surgical Craniectomy: A Computer Modeling Study," PLOS ONE, vol. 11, No. 10, p. e0164051, Oct. 2016.
Miranda et al., "Predicting the electric field distribution in the brain for the treatment of glioblastoma," Physics in Medicine & Biology, vol. 59, pp. 4137-4147, Jul. 2014.
European Search Report issued in application EP 22180751 dated Oct. 10, 2022.

* cited by examiner

APPLYING TUMOR TREATING FIELDS (TTFIELDS) VIA ELECTRODES EMBEDDED INTO SKULL IMPLANTS

CROSS REFERENCE TO RELATED APPLICATIONS

This Application claims the benefit of U.S. Provisional Application 62/880,893, filed Jul. 31, 2019, which is incorporated herein by reference in its entirety.

BACKGROUND

Tumor Treating Fields, or TTFields, are low intensity (e.g., 1-3 V/cm) alternating electric fields within the intermediate frequency range (e.g., 100-500 kHz) that inhibit cancer cell growth. This non-invasive treatment targets solid tumors and is described in U.S. Pat. No. 7,565,205, which is incorporated herein by reference in its entirety. 200 kHz TTFields are FDA approved for the treatment of glioblastoma (GBM), and may be delivered, for example, via the Optune™ system. Optune™ includes a field generator and two pairs of transducer arrays (i.e., electrode arrays) that are placed on the patient's shaved head. One pair of arrays is positioned to the left and right of the tumor, and the other pair of arrays is positioned anterior and posterior to the tumor.

SUMMARY OF THE INVENTION

One aspect of the invention is directed to a first apparatus. The first apparatus comprises a rigid substrate shaped and dimensioned to replace a section of a skull. The substrate has an inner side and an outer side. The first apparatus also comprises an electrically conductive plate having an inner side and an outer side. The outer side of the plate is affixed to the inner side of the substrate. The first apparatus also comprises a dielectric layer disposed on the inner side of the plate; and an electrically conductive lead having an inner end and an outer end. The inner end of the lead is disposed in electrical contact with the plate, the lead passes through the substrate, and the outer end of the lead is configured to accept an electrical signal from an external device.

Some embodiments of the first apparatus further comprise a temperature sensor positioned adjacent to the dielectric layer. Optionally, these embodiments may further comprise at least one wire that passes through the substrate and terminates at the temperature sensor, wherein the wire is configured to transmit an electrical signal from the temperature sensor to the external device. Optionally, in these embodiments, the temperature sensor comprises a thermistor.

In some embodiments of the first apparatus, the dielectric layer comprises a ceramic layer with a dielectric constant of at least 10,000. In some embodiments of the first apparatus, the dielectric layer comprises a flexible thin layer of high dielectric polymer.

Another aspect of the invention is directed to a second apparatus. The second apparatus comprises a rigid substrate shaped and dimensioned to replace a section of a skull. The substrate has an inner side and an outer side. The second apparatus also comprises a plurality of electrically conductive plates, each having an inner side and an outer side. The outer side of each plate is affixed to the inner side of the substrate. The second apparatus also comprises a dielectric layer disposed on the inner side of each plate; and a first electrically conductive lead having an inner end and an outer end. The inner end of the first lead is disposed in electrical contact with a first one of the plates, the first lead passes through the substrate, and the outer end of the first lead is configured to accept an electrical signal from an external device.

Some embodiments of the second apparatus further comprise a second electrically conductive lead having an inner end and an outer end. The inner end of the second lead is disposed in electrical contact with a second one of the plates, the second lead passes through the substrate, and the outer end of the second lead is configured to accept an electrical signal from the external device.

Some embodiments of the second apparatus further comprise an additional electrically conductive lead disposed to electrically connect the first one of the plates with a second one of the plates.

Some embodiments of the second apparatus further comprise a temperature sensor positioned adjacent to the dielectric layer. Optionally, these embodiments may further comprise at least one wire that passes through the substrate and terminates at the temperature sensor, wherein the wire is configured to transmit an electrical signal from the temperature sensor to the external device. Optionally, in these embodiments, the temperature sensor comprises a thermistor.

In some embodiments of the second apparatus, the dielectric layer comprises a ceramic layer with a dielectric constant of at least 10,000. In some embodiments of the second apparatus, the dielectric layer comprises a flexible thin layer of high dielectric polymer.

Another aspect of the invention is directed to a first method of treating a tumor in a person's head. The first method comprises positioning a first set of electrodes on an inner side of a first skull implant on a first side of the tumor; positioning a second set of electrodes on a second side of the tumor that is opposite to the first side; and applying an AC voltage between the first set of electrodes and the second set of electrodes to generate an alternating electric field that passes through the tumor.

In some instances of the first method, the second set of electrodes is positioned on an inner side of the first skull implant. In some instances of the first method, the second set of electrodes is positioned on an inner side of a second skull implant. In some instances of the first method, the second set of electrodes is positioned on an exterior surface of the person's head.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

In a patient with glioblastoma, when the Optune™ transducer arrays are positioned on a patient's shaved head, the electric field must pass through the patient's scalp and skull twice in order to reach the tumor. This situation introduces two problems. First, the presence of the skull between the transducer array and the tumor makes it more difficult to aim the field at the desired location (i.e., the tumor bed) in the brain. And second, due to attenuation of the electric field introduced by the skull and scalp, the voltage and current that is applied to the transducer arrays must be relatively high (e.g., on the order of 50 VAC and on the order of 1 A) in order to obtain an electric field with a therapeutically effective magnitude in the tumor bed.

Figure 1:
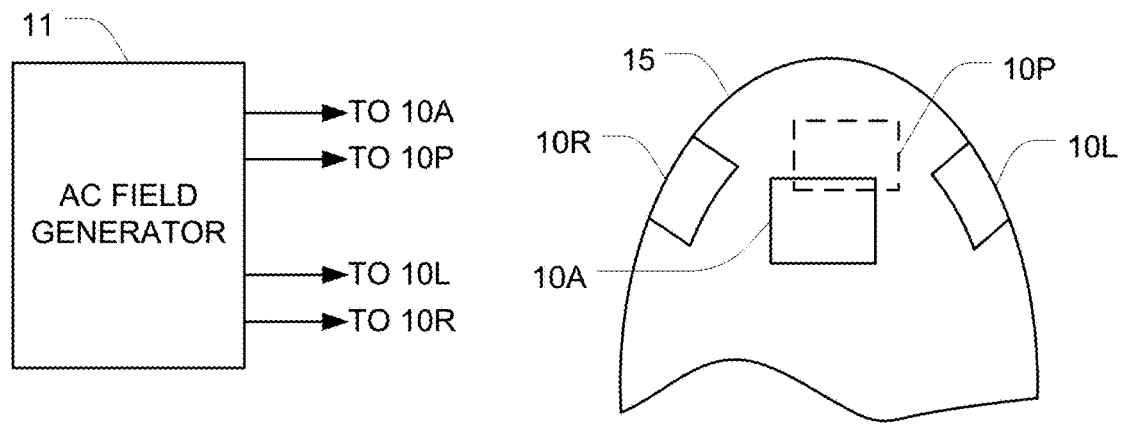
FIG. 1 depicts an embodiment that incorporates transducer arrays into four skull implants.

FIG. 1 depicts an embodiment that ameliorates both these problems by incorporating transducer arrays into one or more skull implants. In the illustrated embodiment, skull implants 10L and 10R are positioned on the left and right sides of the patient's skull 15, respectively; and skull implants 10A and 10P are positioned on the anterior and posterior sides of the patient's skull 15, respectively. An AC field generator 11 (a) applies an AC voltage between the electrodes in skull implant 10A and the electrodes in skull implant 10P for a first interval of time (e.g., 1 second); then (b) applies an AC voltage between the electrodes in skull implant 10L and the electrodes in skull implant 10R for a second interval of time (e.g., 1 second); then repeats that two-step sequence (a) and (b) for the duration of the treatment.

Figure 2:
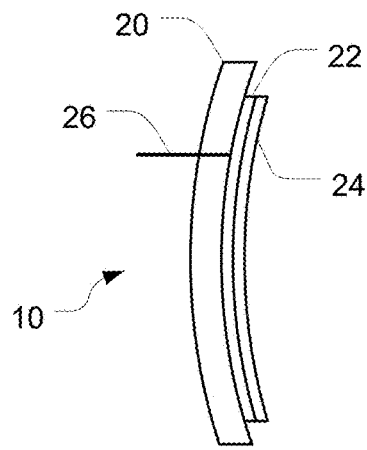
FIG. 2 depicts a first embodiment for implementing any one of the skull implants depicted in FIG. 1.

FIG. 2 depicts a first embodiment for implementing any one of the skull implants 10A/P/L/R depicted in FIG. 1. In this embodiment, a rigid substrate 20 is shaped and dimensioned to replace a section of a skull. The substrate 20 has an inner side and an outer side, and may be formed using any of a variety of conventional approaches for forming a skull implant (including but not limited to 3D printing). In some preferred embodiments, the substrate 20 has an area of at least 5 cm$^2$.

An electrically conductive plate 22 is affixed to the inner side of the substrate 20. This plate 22 is preferably metal (e.g., copper, steel, etc.), but alternative conductive materials may also be used. The shape of the plate 22 may be customized to match the contours of the substrate 20, and the outer side of the plate 22 may be affixed to the substrate 20 using any of a variety of conventional approaches including but not limited to 3D printing and adhesives. A dielectric layer 24 is disposed on the inner side of the plate 22.

In many situations, it is preferable to capacitively coupled the electric field into the target region. The conductive plate 22 and the dielectric layer 24 form a capacitor, and using a higher capacitance improves the coupling of the electric field into the tumor. One approach for achieving a high capacitance is to use a ceramic dielectric material with a dielectric constant of at least 10,000 for implementing the dielectric layer 24, similar to the approach used in the conventional Optune™ system. An alternative approach for increasing the capacitance is to use a flexible thin layer of high dielectric polymer as the dielectric layer 24.

Any portion of the conductive plate 22 that is not covered by the dielectric 24 should be covered by an appropriate insulator (e.g., medical grade silicone) to prevent non-capacitive coupling between the conductive plate 22 and tissue in the patient's head.

The inner end of an electrically conductive lead 26 (e.g., a wire) is disposed in electrical contact with the plate 22. The lead 26 passes through the substrate 20, and the outer end of the lead 26 is configured to accept an electrical signal from an external device (e.g., the field generator 11 depicted in FIG. 1). This may be accomplished, for example, by providing a terminal at the outer end of the lead 26.

Assume, for example, that four sets of the apparatus 10 depicted in FIG. 2 are positioned on all four sides of the patient's head, (i.e., left, right, anterior, and posterior, respectively), as depicted in FIG. 1. The field generator 11 generates an AC voltage on the wires that lead to implant 10A and 10P, then generates an AC voltage on the wires that lead to implants 10L and 10R (in a repeating and alternating sequence as described above). A corresponding AC current will travel through the wires 26 until it reaches the conductive plate 22 in each of the implants 10A/B/L/R. Due to the presence of the dielectric layers 24, the desired electric field will be imposed in the tumor bed via capacitive coupling.

Preferably, at least one temperature sensor (e.g. a thermistor, not shown) is integrated into each implant 10A/P/L/R to reduce the risk of overheating any portion of the patient's brain. In some embodiments, appropriate wiring (not shown) passes through the substrate 20 and is used to route the signal from the temperature sensor to the system's controller (which may be located, for example, in the field generator 11 shown in FIG. 1). In alternative embodiments, the system may be configured to communicate with the temperature sensor wirelessly using any of a variety of conventional approaches.

Figure 3:
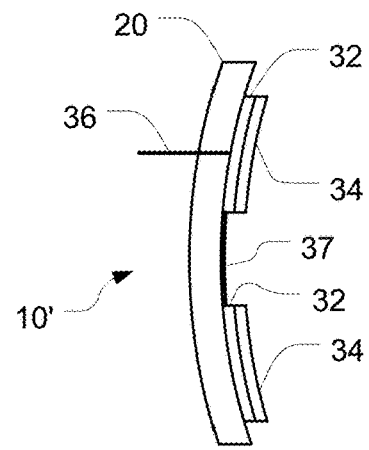
FIG. 3 depicts a second embodiment for implementing any one of the skull implants depicted in FIG. 1.

FIG. 3 is similar to the FIG. 2 embodiment, except that instead of using a single conductive plate 22 and a single dielectric layer 24 (as in the FIG. 2 embodiment), a plurality of smaller conductive plates 32 and smaller dielectric layers 34 are used. Optionally, each of these smaller conductive plates 32 may be round. Optionally, each of the smaller dielectric layers 34 may be a ceramic coating disposed on the smaller conductive plate 32.

Figure 4:
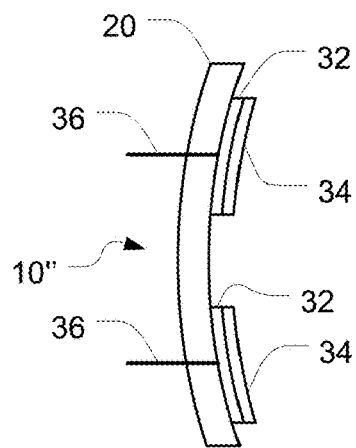
FIG. 4 depicts a third embodiment for implementing any one of the skull implants depicted in FIG. 1.

In the FIG. 3 embodiment, a single lead 36 passes through the substrate 20 to one of the conductive plates 32, and internal wiring 37 is used to route the current to the other conductive plates. Alternatively, as depicted in FIG. 4, the internal wiring may be omitted if each of the conductive plates 32 is provided with its own lead 36 that passes through the substrate 20.

Notably, since the electric field does not have to pass through the scalp or skull, the voltage and current used in this embodiment can be significantly lower than the voltage and current used in the conventional Optune™ system for any given desired field strength at the tumor. (This is because in the conventional Optune™ system, the electrodes are all positioned on the shaved scalp of the patient, which means that the electric field must traverse the scalp and skull twice to reach the tumor.)

In addition, when the transducer arrays are incorporated into skull implants, the planning of treatment so that the desired field appears in the tumor bed may be simplified because the electrical path between the transducer arrays on opposite sides of the tumor is simplified. Finally, incorporating transducer arrays into skull implants can improve treatment planning in situations where the position of a surgical wound or skin abnormalities might prevent the application of conventional Optune™ transducer arrays to particular places on the surface of a patient's skin.

Note that FIG. 1 depicts that all of the electrodes are incorporated into respective skull implants 10A/P/L/R. But in alternative embodiments, only some sets of electrodes are incorporated into a skull implant, and the remaining sets of electrodes are positioned outside the patient's skull (as in conventional TTFields treatment using Optune™). For example, one set of electrodes could be positioned in a skull implant 10A on the anterior side of the patient's head, and the sets of electrodes on the right, left, and posterior sides could all be positioned outside the patient's skull.

In other alternative embodiments, two or more sets of electrodes are incorporated into a single skull implant. For example, a single roughly hemispherical skull implant could be installed on a patient's head in place of the top hemisphere of the patient's skull, and all four sets of electrodes could be incorporated into that single skull implant (i.e., on the left, right, anterior, and posterior inner walls of the implant).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus comprising
    a rigid substrate shaped and dimensioned to replace a section of a skull, the substrate having an inner side and an outer side opposed to the inner side;
    an electrically conductive plate having an inner side and an outer side, wherein the outer side of the plate is affixed to the inner side of the substrate;
    a dielectric layer disposed on the inner side of the plate; and
    an electrically conductive lead having an inner end and an outer end, wherein the inner end of the lead is disposed in electrical contact with the plate, wherein the lead passes through the substrate from a point on the inner side of the substrate to a point on the outer side of the substrate, and wherein the outer end of the lead extends outwardly from the outer side of the substrate and is configured to accept an electrical signal from an external device.

2. The apparatus of claim 1, further comprising a temperature sensor positioned adjacent to the dielectric layer.

3. The apparatus of claim 2, further comprising at least one wire that passes through the substrate and terminates at the temperature sensor, wherein the wire is configured to transmit an electrical signal from the temperature sensor to the external device.

4. The apparatus of claim 3, wherein the temperature sensor comprises a thermistor.

5. The apparatus of claim 1, wherein the dielectric layer comprises a ceramic layer with a dielectric constant of at least 10,000.

6. The apparatus of claim 1, wherein the dielectric layer comprises a flexible thin layer of high dielectric polymer.

7. An apparatus comprising:
    a rigid substrate shaped and dimensioned to replace a section of a skull, the substrate having an inner side and an outer side opposed to the inner side;
    a plurality of electrically conductive plates, each having an inner side and an outer side, wherein the outer side of each plate is affixed to the inner side of the substrate;
    a dielectric layer disposed on the inner side of each plate; and
    a first electrically conductive lead having an inner end and an outer end, wherein the inner end of the first lead is disposed in electrical contact with a first one of the plates, wherein the first lead passes through the substrate from a first point on the inner side of the substrate to a second point on the outer side of the substrate, and wherein the outer end of the first lead extends outwardly from the outer side of the substrate and is configured to accept an electrical signal from an external device.

8. The apparatus of claim 7, further comprising a second electrically conductive lead having an inner end and an outer end, wherein the inner end of the second lead is disposed in electrical contact with a second one of the plates, wherein the second lead passes through the substrate from a third point on the inner side of the substrate to a fourth point on the outer side of the substrate, and wherein the outer end of the second lead is configured to accept an electrical signal from the external device.

9. The apparatus of claim 7, further comprising an additional electrically conductive lead disposed to electrically connect the first one of the plates with a second one of the plates.

10. The apparatus of claim 7, further comprising a temperature sensor positioned adjacent to the dielectric layer.

11. The apparatus of claim 10, further comprising at least one wire that passes through the substrate and terminates at the temperature sensor, wherein the wire is configured to transmit an electrical signal from the temperature sensor to the external device.

12. The apparatus of claim 11, wherein the temperature sensor comprises a thermistor.

13. The apparatus of claim 7, wherein the dielectric layer comprises a ceramic layer with a dielectric constant of at least 10,000.

14. The apparatus of claim 7, wherein the dielectric layer comprises a flexible thin layer of high dielectric polymer.

* * * * *